United States Patent
Odanaka et al.

(10) Patent No.: US 9,610,146 B2
(45) Date of Patent: Apr. 4, 2017

(54) DENTAL BLOCK

(71) Applicant: GC Corporation, Tokyo (JP)

(72) Inventors: Yasuhiro Odanaka, Tokyo (JP); Yuki Sakamoto, Tokyo (JP)

(73) Assignee: GC Corporation, Tokyo (JP)

(*) Notice: Subject to any disclaimer, the term of this patent is extended or adjusted under 35 U.S.C. 154(b) by 35 days.

(21) Appl. No.: 14/413,744

(22) PCT Filed: Jun. 17, 2013

(86) PCT No.: PCT/JP2013/066572
§ 371 (c)(1),
(2) Date: Jan. 9, 2015

(87) PCT Pub. No.: WO2014/013824
PCT Pub. Date: Jan. 23, 2014

(65) Prior Publication Data
US 2015/0164622 A1 Jun. 18, 2015

(30) Foreign Application Priority Data
Jul. 19, 2012 (JP) .................................. 2012-160571

(51) Int. Cl.
*A61C 13/00* (2006.01)
*A61C 8/00* (2006.01)

(52) U.S. Cl.
CPC .......... *A61C 13/0022* (2013.01); *A61C 8/005* (2013.01); *A61C 8/006* (2013.01)

(58) Field of Classification Search
None
See application file for complete search history.

(56) References Cited

U.S. PATENT DOCUMENTS 6,788,986 B1    9/2004  Traber et al.
2007/0128580 A1  6/2007  Mormann
(Continued)

FOREIGN PATENT DOCUMENTS

JP  2001-054525  2/2001
JP  2007-502178  2/2007
(Continued)

OTHER PUBLICATIONS

International Search Report mailed on Jul. 16, 2013.

*Primary Examiner* — David Sample
*Assistant Examiner* — Nicholas W Jordan
(74) *Attorney, Agent, or Firm* — IPUSA, PLLC

(57) ABSTRACT

A dental block includes a block body having a one surface, and an engagement portion to be engaged with a dental implant fixture. The engagement portion has a bolt through hole and is formed in the one surface of the block body. The dental block further includes a ring-shaped abutment surface to be abutted against a top surface on the oral cavity inner side of the dental implant fixture. The ring-shaped abutment surface is positioned more inside the block body than the one surface and is formed from an end portion positioned at the most oral cavity inner side of the engagement portion to surround the end portion, and to be parallel to the one surface of the block body. The dental block further includes a diameter-enlarged portion having a tapered shape whose diameter increases from the ring-shaped abutment surface toward the one surface of the block body.

1 Claim, 3 Drawing Sheets

CUTTING PROCESS

(56) References Cited

U.S. PATENT DOCUMENTS

2008/0254413 A1* 10/2008 Gampert ............ A61C 13/0022
433/223
2010/0323324 A1  12/2010 Kim

FOREIGN PATENT DOCUMENTS

| JP | 2007-519467 | 7/2007 |
| JP | 2007-222225 | 9/2007 |
| JP | 2010-518991 | 6/2010 |
| KR | 10-2011-0026166 | 3/2011 |
| WO | 2005/072639 | 8/2005 |
| WO | 2008/103908 | 8/2008 |

* cited by examiner

CUTTING PROCESS

CUTTING PROCESS

DENTAL BLOCK

TECHNICAL FIELD

The present invention relates to a dental block by which, when a gap is formed between the gum and a dental abutment due to recession of the gum after fixing a dental prosthesis in an oral cavity by using a dental implant system, a cutting process can be easily performed on a new dental abutment for covering the gap.

BACKGROUND ART

There is a treatment method that is becoming popular, which is for recovering an oral function that has been lost at a defective tooth part. This treatment method uses a dental implant system for fixing a dental prosthesis on the oral cavity inner side of a dental implant fixture that is embedded into the jawbone at the defective tooth part to act as an artificial dental root that is directly connected to the jawbone. This dental implant system typically has a structure in which a dental abutment, which pierces through the gum, is arranged on the oral cavity inner side of the dental implant fixture, and the dental prosthesis is arranged on the oral cavity inner side of this dental abutment.

The gum tissue after a tooth is extracted at the part that is treated by using the above dental implant system, has a feature of having less fibroblast cells compared to that of the gum before the tooth is extracted. Thus, germs can easily enter the jawbone from between the periphery of the dental abutment and the gum. Furthermore, the ability of restoring the tissue that has been destroyed by inflammation is low, which tends to be the factor of causing bone absorption to proceed.

Furthermore, the gum tissue (collagen tissue) in the gum before extracting the tooth is reproduced so as to be orthogonal with respect to the natural tooth. Meanwhile, in the tissue that is reproduced after embedding the dental implant fixture, the gum tissue is reproduced so as to be parallel to the dental implant fixture. The gum tissue parallel to the dental implant fixture is weakly combined with the contacting dental implant fixture and the contacting dental abutment, and therefore gum recession is likely to occur.

When the gum recession occurs as described above, the leading end side of the gum contacting the dental abutment recedes, and germs enter into the jawbone, which often causes bone absorption and reduces the sensuousness. As a measure for such a problem, there is a transmucosal element (dental abutment or spacer), which is provided with a groove or a recessed part that extends entirely or partially around its periphery, in order to integrate the gum and the transmucosal element (see, for example, Patent Document 1, claim 8). This groove is formed to increase the stability of the surrounding gum. However, as described above, the gum tissue after extracting the tooth has a different scar tissue from that of the gum tissue before extracting the tooth. Therefore, even if an attempt is made to integrate the gum and the transmucosal element by providing a groove, it is difficult to achieve the same effects as those of the gum tissue before extracting the tooth.

As a countermeasure for the problem of the difficulty in preventing the gum recession as described above, there is a method of fabricating a new dental abutment having a rim part that can cover the gap formed between the gum and the dental abutment, directly using the dental implant fixture that is already embedded in the jawbone, and newly applying this new dental abutment and the dental prosthesis thereof. This method is the most practical countermeasure because the sensuousness is not reduced and the procession of bone absorption can be delayed.

Generally, as a dental abutment, there is a type having a ready-made form prepared by each implant manufacturer, and there is a type that is fabricated from a dental block prepared in advance, by a device that is mechanized/automated by a CAD/CAM system. An example of a frequently used dental block has a substantially rectangular parallelepiped shape, in which an engagement portion for engaging with a dental implant fixture that is commonly required for dental abutments that have been cut into any shape, and a bolt through hole for inserting a bolt that is required for engaging the dental abutment with the dental implant fixture, are formed in advance.

However, before the gum recedes, the surface where the dental abutment abuts against the gum has a shape that is warped up toward the oral cavity inner side (FIG. 8); however, after the gum has receded, the surface where the dental abutment abuts against the gum has a shape that is directed downward toward the residual ridge side (FIG. 6). Therefore, it is difficult to fabricate a dental abutment for before gum recession and a dental abutment for after gum recession, from dental blocks having the same shape.

That is to say, as for a dental abutment before gum recession, it is easy to fabricate a dental abutment in which the surface that abuts against the gum has a shape that is warped up toward the oral cavity inner side, by using a dental block in which the engagement portion which engages with the dental implant fixture is provided in a protruding condition in advance, and simply cutting the part near the engagement portion, for example as illustrated in FIG. 7. However, by a dental block as illustrated in FIG. 7, it is not possible to perform a cutting process from the part near the engagement portion which engages with the dental implant fixture, such that the part to cover the part where the gum has receded, is in a protruding condition. Therefore, unless a significant process is performed, such as processing the entire dental block again including the engagement portion which engages with the dental implant fixture, it is not possible to form a dental abutment for after gum recession by cutting a conventional dental block as described above.

PRIOR ART DOCUMENTS

Patent Documents

Patent Document 1: Japanese National Publication of International Patent Application No. 2007-519467

DISCLOSURE OF THE INVENTION

Problem to be Solved by the Invention

In view of the above problems, an object of the present invention is to provide a dental block by which, when a gap is formed between the gum and a dental abutment due to the recession of the gum after fixing a dental prosthesis by using a dental implant system, a cutting process can be easily performed on a new dental abutment for covering the gap part.

Means of Solving the Problem

As a result of diligent research conducted to solve the problem described above, the present inventors found that even when the gum recedes and moves downward toward the jawbone side, the position of the jawbone does not change. Therefore, when a dental implant fixture that is already embedded in the jawbone is directly used, as a result, the leading end of the gum that has receded will be at a position that has moved downward toward the jawbone side from the top surface of the oral cavity inner side of the dental implant fixture. Therefore, when fabricating a new dental abutment, the new dental abutment needs to be formed such that the rim part thereof protrudes toward the jawbone side more than the top surface on the oral cavity inner side of the dental implant fixture so as to cover the jawbone part where the gum has been receded and removed. Therefore, by forming a part (ring-shaped abutment surface) that abuts against the top surface on the oral cavity inner side of the dental implant fixture inside the dental block body (block body), and further forming a diameter-enlarged portion having a tapered shape whose diameter increases from the ring-shaped abutment surface toward one surface of the block body being a plane, it is possible to easily cover the jawbone part where the gum has been receded and removed by performing a cutting process on the block part including this diameter-enlarged portion, because the diameter-enlarged portion continuing from the ring-shaped abutment surface is formed toward the outside. Furthermore, by making this diameter-enlarged portion to have a tapered shape, the diameter-enlarged portion has a shape that extends along the shape of the jawbone part where the gum has been receded and removed, and therefore, there may be cases where the cutting process on the part to be abutted against the jawbone can be omitted, or only a slight cutting process would suffice. Thus, the operation can be performed efficiently and easily. The present invention has been completed upon ascertaining this effect.

That is to say, the present invention is a dental block to be subjected to a cutting process to form a dental abutment including: a block body having a one surface being a plane; an engagement portion to be inserted in and engaged with a dental implant fixture, the engagement portion having a bolt through hole and being formed in the one surface of the block body; the dental block further including: a ring-shaped abutment surface to be abutted against a top surface on the oral cavity inner side of the dental implant fixture, the ring-shaped abutment surface being positioned more inside the block body than the one surface of the block body, being formed from an end portion positioned at the most oral cavity inner side of the engagement portion to surround the end portion, and being parallel to the one surface of the block body; and a diameter-enlarged portion having a tapered shape whose diameter increases from the ring-shaped abutment surface toward the one surface of the block body.

Effects of the Invention

The dental block according to the present invention is a dental block to be subjected to a cutting process to form a dental abutment including: a block body having a one surface being a plane, and an engagement portion to be inserted in and engaged with a dental implant fixture, the engagement portion having a bolt through hole and being formed in the one surface of a block body, the dental block further including: a ring-shaped abutment surface to be abutted against a top surface on the oral cavity inner side of the dental implant fixture, the ring-shaped abutment surface being positioned more inside the block body than the one surface of the block body, being formed from an end portion positioned at the most oral cavity inner side of the engagement portion to surround the end portion, and being parallel to the one surface of the block body; and a diameter-enlarged portion having a tapered shape whose diameter increases from the ring-shaped abutment surface toward the one surface of the block body, and the diameter-enlarged portion continuing from the ring-shaped abutment surface is formed toward the outside. Therefore, by performing a cutting process on this block body including the diameter-enlarged portion, it is possible to easily cover the jawbone part where the gum has been receded and removed. Furthermore, this diameter-enlarged portion has a tapered shape, and the diameter-enlarged portion has a shape that extends along the shape of the jawbone part where the gum has been receded and removed, and therefore, there may be cases where the cutting process on the part to be abutted against the jawbone can be omitted, or only a slight cutting process would suffice. Thus, the operation can be performed efficiently and easily. Furthermore, when the dental implant fixture has been embedded in an inclined manner in the jawbone due to clinical restrictions, an angle may be formed between the axis of the direction of embedding the dental implant fixture and the axis of the dental abutment. In this case also, a gap may be formed between the gum and the dental abutment. The dental block according to the present invention can also be effectively used for such a case.

MODE OF CARRYING OUT THE INVENTION

Figure 1:
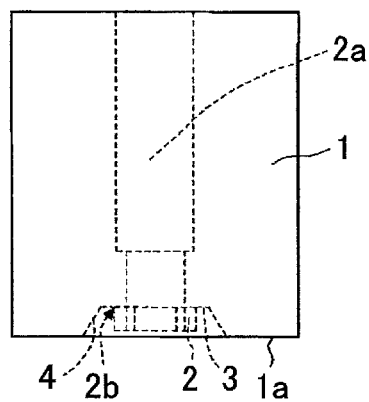
FIG. 1 is a front view indicating an embodiment of a dental block according to the present invention.
Figure 2:
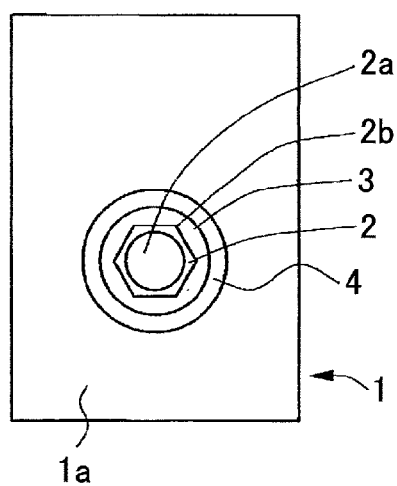
FIG. 2 is a bottom view of the dental block of FIG. 1.
Figure 3:
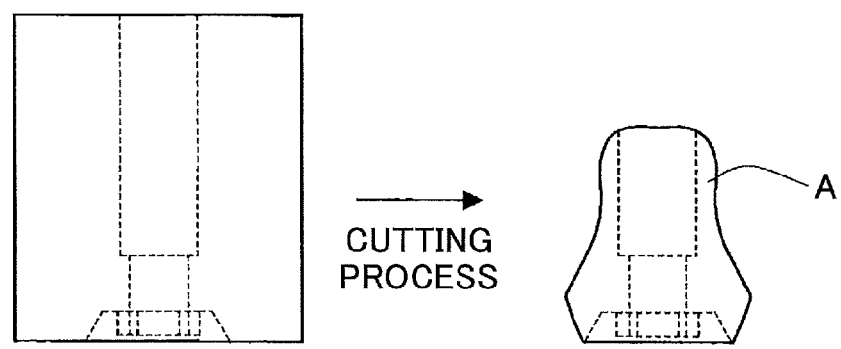
FIG. 3 is an explanatory diagram indicating a dental abutment that has been formed by performing a cutting process on the dental block of FIG. 1.
Figure 4:
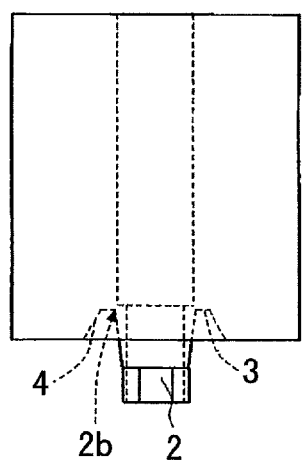
FIG. 4 is a front view of another embodiment of the dental block according to the present invention.

A detailed description will hereinafter be given of the dental block according to the present invention, by referring to the drawings.

A denotes a dental abutment, and F denotes a dental implant fixture with which the dental abutment A is engaged.

A block body 1 is subjected to a cutting process to form the dental abutment A, and which includes a one surface 1a being a plane. The block body 1 may have a substantially rectangular parallelepiped shape as illustrated in FIGS. 1 to 4; however, as long as the one surface 1a is a plane, the other surfaces may be curved surfaces. Furthermore, a gripper may also be provided such that the block body 1 can be gripped by a measuring device or a processing device in the CAD/CAM system.

An engagement portion 2, which is formed in the one surface 1a of the block body 1, includes a bolt through hole 2a, and the engagement portion 2 is inserted in and engaged with the dental implant fixture F. The engagement portion 2 may have an overall shape that is a hexagonal cylinder as illustrated in, for example, FIGS. 1 to 4, or although not illustrated, the engagement portion 2 may have, for example, an overall cylindrical shape having a projection formed on the side of the cylinder, etc. When the engagement portion 2 is a hexagonal cylinder or a cylinder, it is preferable in that the engagement portion 2 can be easily positioned with respect to the dental implant fixture F with which the engagement portion 2 is engaged, and that the engagement portion 2 can be easily processed. However, the shape of the engagement portion 2 is not necessarily limited to those described above; the engagement portion 2 may be any shape as long as the engagement portion 2 can be inserted in and engaged with the dental implant fixture F that is embedded in the jawbone.

A ring-shaped abutment surface 3, which is positioned more inside the block body 1 than the one surface 1a of the block body 1, and is formed from an end portion 2b positioned at the most oral cavity inner side of the engagement portion 2 to surround the end portion 2b, and is parallel to the one surface 1a of the block body 1, and is to be abutted against a top surface Fa on the oral cavity inner side of the dental implant fixture F. The dental implant fixture F that is embedded and fixed in the jawbone, may have a substantially cylindrical shape or a substantially cylindrical shape having a tapered shape. On the oral cavity inner side of the dental implant fixture F, an engagement hole is provided so that the engagement portion 2 of the dental abutment A is inserted in and engaged with. The top surface Fa on the oral cavity inner side of the dental implant fixture F is formed between this engagement hole and the outer periphery on the oral cavity inner side of the dental implant fixture F, and the top surface Fa on the oral cavity inner side has a ring shape. In order to be abutted against this ring-shaped top surface Fa, the ring-shaped abutment surface 3 is formed in advance in the dental block according to the present invention. A feature of the dental block according to the present invention is that the ring-shaped abutment surface 3 is formed so as to be positioned more inside the block body 1 than the one surface 1a.

A diameter-enlarged portion 4 having a tapered shape whose diameter increases from the ring-shaped abutment surface 3 toward the one surface 1a of the block body 1. The diameter-enlarged portion 4 having a tapered shape whose diameter increases, can easily cover the jawbone part where the gum has been receded and removed. Furthermore, by making this diameter-enlarged portion 4 to have a tapered shape, the diameter-enlarged portion 4 has a shape that extends along the shape of the jawbone part where the gum has been receded and removed. Therefore, there are many cases where the cutting process on the part to be abutted against the jawbone can be omitted, or only a slight cutting process would suffice. Thus, the operation can be performed efficiently and easily.

In order to actually fabricate the dental block according to the present invention as described above, first, as illustrated in FIG. 1 or 5, the bolt through hole 2a is drilled into the one surface 1a of the block body 1 having, for example, a rectangular parallelepiped shape, such that the shaft center of the bolt through hole 2a is perpendicular. This bolt through hole 2a is formed as in the embodiments of FIG. 1 or FIG. 5, to have a part having a large diameter through which the head of the bolt can be passed, and a part having a small diameter that is smaller than the head of the bolt. Accordingly, the head of the bolt that is passed through the bolt through hole 2a is engaged at the step part between the part having a large diameter and the part having a small diameter, and by simply threading this bolt into the dental implant fixture embedded in the jawbone, it is possible to firmly fix the dental abutment. Note that the bolt through hole 2a can have a fixed shape regardless of the patient, and therefore a dental block, in which this bolt through hole 2a is formed in advance, may be used.

Next, the periphery of this bolt through hole 2a is drilled from the one surface 1a of the block body 1, to form the engagement portion 2 to be engaged with the dental implant fixture F. By drilling the bolt through hole 2a as described above, the end portion 2b positioned at the most oral cavity inner side of the engagement portion 2 can be positioned more inside the block body 1 than the one surface 1a, and the ring-shaped abutment surface 3 to be abutted against the top surface Fa on the oral cavity inner side of the dental implant fixture F can be formed. Furthermore, when drilling the bolt through hole 2a as described above, by drilling the bolt through hole 2a so as to have a tapered shape whose diameter increases toward the one surface 1a of the block body 1, the diameter-enlarged portion 4 can also be formed, and the dental block according to the present invention can be easily fabricated as described above.

Figure 5:
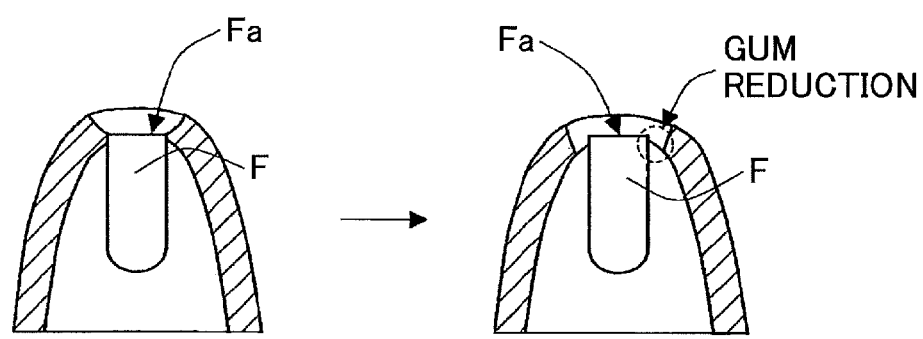
FIG. 5 is a schematic explanatory diagram indicating before and after the recession of the gum.
Figure 6:
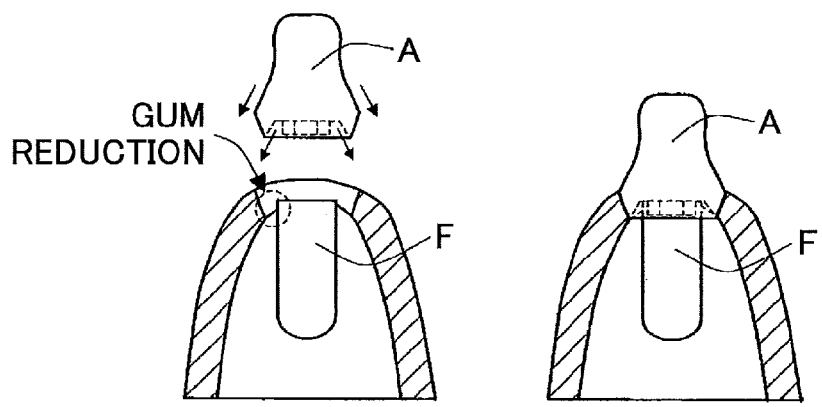
FIG. 6 is a schematic explanatory diagram indicating a state where the dental abutment, which has been formed by performing a cutting process on the dental block according to the present invention of FIG. 3, is engaged with the part where the gum has receded as illustrated in FIG. 5.
Figure 7:
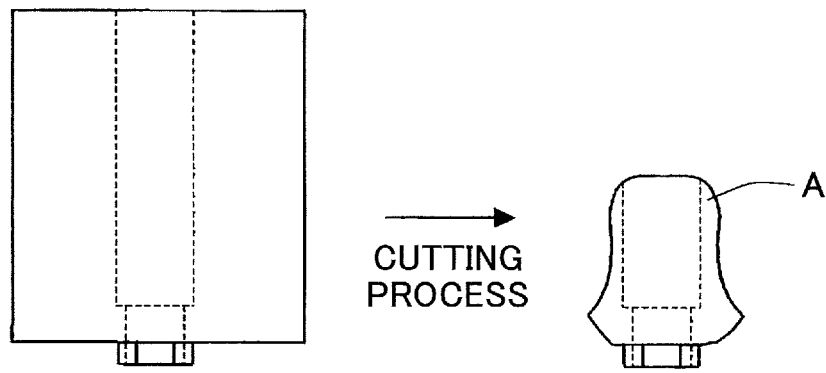
FIG. 7 is an explanatory diagram indicating a conventional dental block and a dental abutment formed by performing a cutting process on the conventional dental block.
Figure 8:
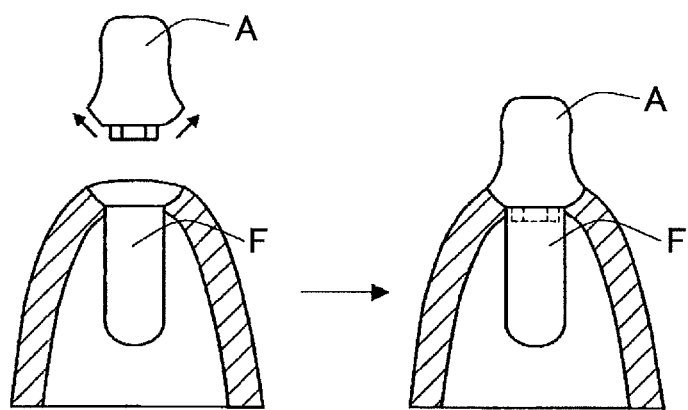
FIG. 8 is a schematic explanatory diagram indicating a state where the dental abutment, which has been formed by performing a cutting process on the conventional dental block of FIG. 7, is engaged with the part where the gum has not receded.

Furthermore, in the dental block according to the present invention, the leading end part of the engagement portion 2 to be on the jawbone side may be positioned to be on the same plane as the one surface 1a of the block body 1, or the engagement portion 2 may be positioned more inside the block body 1 than the one surface 1a as illustrated in FIG. 1, or the leading end of the engagement portion 2 may be positioned in a state to be protruding more outside of the block body 1 than the one surface 1a as illustrated in FIG. 5. The position of the leading end part of the engagement portion 2 on the jawbone side may be appropriately determined according to the purpose.

Note that as illustrated in FIG. 1, in order to position the engagement portion 2 more inside the block body 1 than the one surface 1a, the cutting process is to be performed such that the leading end part of the engagement portion 2 is cut off at the final stage. Furthermore, as illustrated in FIG. 5, in order to position the leading end of the engagement portion 2 in a state to be protruding more outside of the block body 1 than the one surface 1a of the block body 1, a final cutting process is to be performed on the part that is more outside than the diameter-enlarged portion 4 of the one surface 1a of the block body 1 such that consequently the leading end of the engagement portion 2 is protruding outside.

In the dental block according to the present invention made as described above, the diameter-enlarged portion 4 that continues from the ring-shaped abutment surface 3 becomes the rim part positioned on the jawbone side more than the top surface Fa on the oral cavity inner side of the dental implant fixture F, and can cover the jawbone part where the gum has been receded and removed. Therefore, it is possible to easily fabricate a dental abutment that can cover the part where the gum has receded as illustrated in, for example, FIG. 3, by using a general CAD/CAM system.

DESCRIPTION OF REFERENCE NUMERALS 1 block body
1a one surface 2 engagement portion
2*a* bolt through hole
2*b* end portion positioned on most oral cavity inner side
3 ring-shaped abutment surface
4 taper-shaped diameter-enlarged portion
A dental abutment
F dental implant fixture
Fa top surface on oral cavity inner side

The invention claimed is:

1. A dental block to be subjected to a cutting process to form a dental abutment comprising:
   a block body having a one surface being a plane, and
   an engagement portion to be inserted in and engaged with a dental implant fixture, the engagement portion having a bolt through hole and being formed in the one surface of the block body,
   the dental block further comprising:
   a ring-shaped abutment surface to be abutted against a top surface on the oral cavity inner side of the dental implant fixture, the ring-shaped abutment surface being positioned more inside the block body than the one surface, being formed from an end portion positioned at the most oral cavity inner side of the engagement portion to surround the end portion, and being parallel to the one surface of the block body, and
   a diameter-enlarged portion having a tapered shape whose diameter increases from the ring-shaped abutment surface toward the one surface of the block body,
   wherein an enlarged end of a tapered portion of the diameter-enlarged portion is connected to the one surface of the block body.

\* \* \* \* \*